(12) United States Patent
Richards

(10) Patent No.: US 9,743,838 B2
(45) Date of Patent: Aug. 29, 2017

(54) CIRCUITS AND METHODS FOR PHOTOPLETHYSMOGRAPHIC SENSORS

(71) Applicant: Fitbit, Inc., San Francisco, CA (US)

(72) Inventor: Peter W. Richards, San Francisco, CA (US)

(73) Assignee: FITBIT, INC., San Francisco, CA (US)

( * ) Notice: Subject to any disclaimer, the term of this patent is extended or adjusted under 35 U.S.C. 154(b) by 0 days.

(21) Appl. No.: 14/873,921

(22) Filed: Oct. 2, 2015

(65) Prior Publication Data

US 2017/0095156 A1   Apr. 6, 2017

(51) Int. Cl.
*A61B 5/1455* (2006.01)
*A61B 5/00* (2006.01)
*A61B 5/024* (2006.01)

(52) U.S. Cl.
CPC ........ *A61B 5/0082* (2013.01); *A61B 5/02416* (2013.01); *A61B 5/02427* (2013.01); *A61B 5/02438* (2013.01); *A61B 5/1455* (2013.01); *A61B 5/14551* (2013.01); *A61B 5/7214* (2013.01); *A61B 2560/0247* (2013.01)

(58) Field of Classification Search
CPC ... A61B 5/024; A61B 5/1455; A61B 5/14551; A61B 5/14552; A61B 5/0002; A61B 5/0059; A61B 5/0205; A61B 5/72; A61B 5/7203; A61B 5/7228; A61B 5/7275
USPC ........ 600/310, 323, 336, 340, 473, 476, 500
See application file for complete search history.

(56) References Cited

U.S. PATENT DOCUMENTS

| | | | | |
|---|---|---|---|---|
| 4,781,195 A | * | 11/1988 | Martin ............... | A61B 5/02416 600/336 |
| 5,632,272 A | * | 5/1997 | Diab .................. | A61B 5/14551 600/323 |
| 5,810,723 A | * | 9/1998 | Aldrich ............. | A61B 5/14551 600/322 |
| 5,853,364 A | * | 12/1998 | Baker, Jr. ........... | A61B 5/14551 600/323 |

* cited by examiner

*Primary Examiner* — Eric Winakur
*Assistant Examiner* — Chu Chuan (JJ) Liu
(74) *Attorney, Agent, or Firm* — Buckley, Maschoff & Talwalkar LLC

(57) ABSTRACT

Some embodiments relate to a device, method, and/or computer-readable medium storing processor-executable process steps to remove a component of a signal corresponding to ambient light in a photoplethysmographic sensor device, including capturing a first detected light signal representing an ambient light at a first time, causing a light emitter to generate a source light signal driven at a first level, capturing a second detected light signal representing the source light signal after interacting with a user's tissue plus the first detected light signal, generating a first output signal based on the second detected light signal adjusted by the first detected light signal, causing the light emitter to generate a source light signal driven at a second level, capturing a third detected light signal representing the source light signal driven at the second level after interacting with the user's skin plus the first detected light signal, and generating a second output signal based on the third detected light signal adjusted by the first detected light signal.

25 Claims, 12 Drawing Sheets

US 9,743,838 B2

CIRCUITS AND METHODS FOR PHOTOPLETHYSMOGRAPHIC SENSORS

BACKGROUND

Field

The embodiments described below relate to the measurement of biometric data. Some embodiments relate to the photoplethysmographic sensors.

Description

Recent consumer interest in personal health has led to a variety of personal health monitoring devices being offered on the market. Such devices, until recently, tended to be complicated to use and were typically designed for use with one activity, e.g., bicycle trip computers.

Recent advances in sensor, electronics, and power source miniaturization have allowed the size of personal health monitoring devices (also referred to herein as "biometric tracking" or "biometric monitoring" devices) to be offered in extremely small sizes that were previously impractical. For example, Fitbit, Inc. produces a number of biometric tracking devices that can have a number of features and elements, such as displays, batteries, sensors, wireless communications capabilities, power sources, and interface buttons, as well as mechanisms for attaching these devices to a pocket or other portion of clothing or to a body part of the wearer, packaged within a small volume.

These devices collect, process and display a large variety of data using a variety of sensors. One type of sensor used in some biometric tracking devices is a heart rate sensor. These heart rate sensors typically operate by emitting light into the skin of the user and then measuring the light reflected or diffused back after the emitted light interacts with the user's skin.

SUMMARY

Some embodiments relate to a device, method, and/or computer-readable medium storing processor-executable process steps to remove a component of a signal corresponding to ambient light. Such embodiments may include capturing a first detected light signal representing an ambient light at a first time, causing a light emitter to generate a source light signal driven at a first level, capturing a second detected light signal representing the source light signal after interacting with a user's tissue plus the first detected light signal, generating a first output signal based on the second detected light signal adjusted by the first detected light signal, causing the light emitter to generate a source light signal driven at a second level, capturing a third detected light signal representing the source light signal driven at the second level after interacting with the user's skin plus the first detected light signal, and generating a second output signal based on the third detected light signal adjusted by the first detected light signal.

In some embodiments, the light emitter is operated to capture a fourth detected light signal representing the source light signal driven at the first level after interacting with the user skin plus the first detected light signal, and to generate a third output signal based on the fourth detected light signal adjusted by the first detected light signal. Pursuant to some embodiments, the first detected light signal is detected by activating a light detector.

Pursuant to some embodiments, the output signals are converted to digital form and provided to a processor for further processing.

Embodiments as described herein provide a number of advantages. For example, embodiments provide accurate optical heart rate measurements to be taken at substantially lower power consumption than prior approaches. Further, embodiments provide a substantial savings in circuit board space requirements and component cost, allowing the use of such embodiments in small form factor devices that are battery powered. Other advantages include improved signal-to-noise ratio (SNR) and enhanced dynamic range for rejecting sources of ambient light such as sunlight.

A more complete understanding of some embodiments can be obtained by referring to the following detailed description and to the drawings appended hereto.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the described embodiments. Various modifications, however, will remain readily apparent to those in the art. A specific example will now be described with reference to the appended figures in order to provide an introduction to various features. Embodiments are not limited to the features or description of this example.

Figure 1:
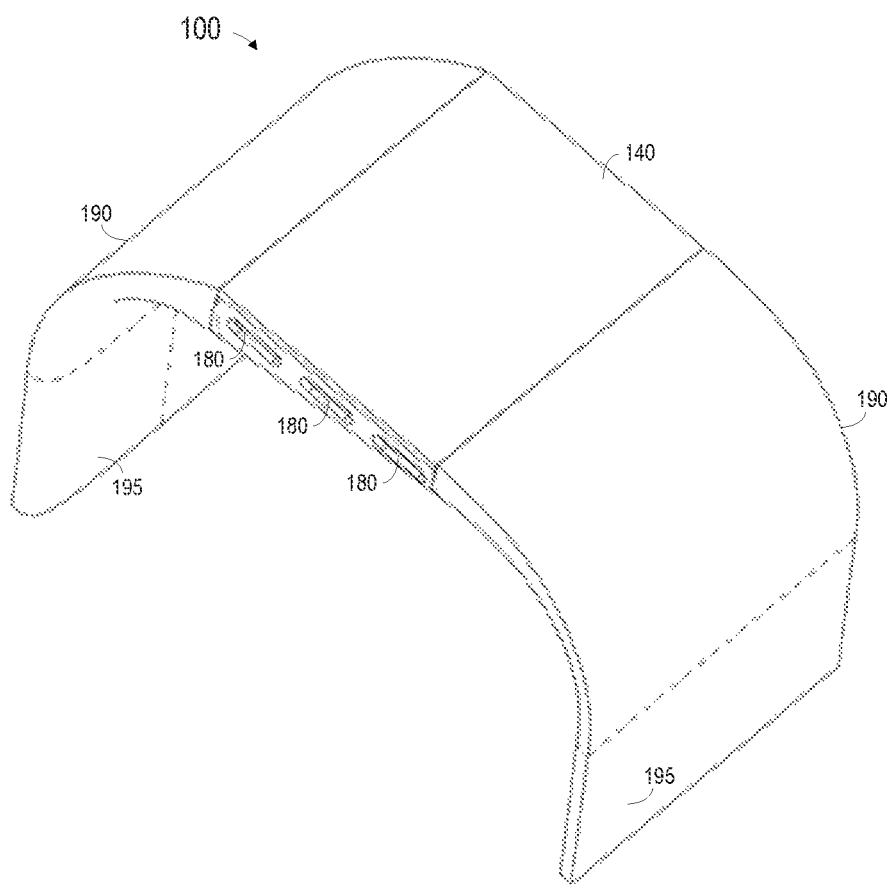
FIG. 1 is a top perspective view of a device according to some embodiments.

As discussed above, a number of biometric monitoring devices are used by consumers, health care professionals, and others who wish to collect and monitor biometric information. An example of such a biometric monitoring device 100 is shown in FIG. 1. According to the illustrated embodiment, the device 100 is wearable on a user's wrist. The device 100 includes a display 140, which may comprise any suitable type of display screen, and which may display graphical indicators based on biometric and other data detected, collected, monitored or otherwise generated by the device 100. The device 100 may include one or more buttons 180 which may be manipulated by a user to provide input to the device 100. The display 140 may also incorporate one or more input devices (such as a touch screen). A band 190 may be wrapped around the wrist and is securable using one or more securing elements 195 (e.g., hook and loop, clasp, shape memory elements, magnets). The shape and configuration of the device 100 is one example configuration within which embodiments of the present invention may be deployed. The photoplethysmographic sensor system and methods set forth herein may be used with desirable results in devices having a wide variety of shapes and configurations, and the shape and configuration illustrated in FIG. 1 and FIG. 2 are for illustrative purposes.

Figure 2:
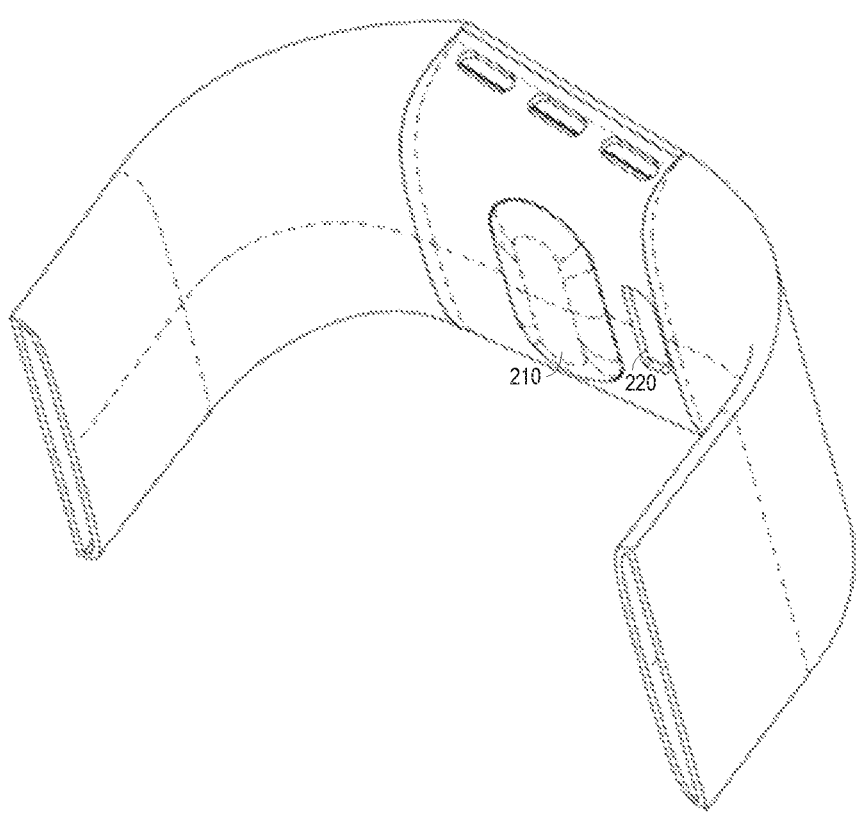
FIG. 2 is a bottom perspective view of a device according to some embodiments.

FIG. 2 is a bottom view of the device 100, showing a sensor component 210 and a power interface 220. The sensor component 210 may include sensors which benefit from close proximity and/or contact with a user's skin. Such sensors may include photoplethysmographic sensors (e.g., heart rate, pulse oximeter, and the like), moisture, temperature, and/or capacitive touch sensors (e.g., to detect when the device is being worn). The power interface 220 may interface with a docking station or other power source to receive electrical charge for charging of batteries located within the device 100. Although a single sensor component 210 is shown for simplicity, multiple sensor components may be provided. Further, while the sensor component 210 is illustrated in FIG. 2 as protruding somewhat from the device 100, other embodiments may place sensors in proximity to the user without use of a distinct protrusion.

Features of a particular category or type of sensor—a "PPG" or "photoplethysmographic" sensor—will be described in further detail herein. PPG sensors, such as a heart rate monitor or pulse oximeter, use a light-based technology to sense pulsating blood flow as controlled by the heart's pumping action. PPG sensors may be used to measure a user's heart rate, blood oxygenation, and other biometric parameters. In the device 100 shown in FIG. 1 and FIG. 2, sensor component 210 may shield or be associated with one or more light sources (e.g., such as light emitting diodes or "LEDs") and light detector(s) and corresponding control circuitry (e.g., as described further below). In some cases, light pipes may be used to optically connect the light source(s) or the detector with the surface of the user's skin. Beneath the skin, the light from the light sources scatters off of blood in the body, some of which may be scattered or reflected back into a photodetector located behind the sensor component 210. In some embodiments, as will be described further herein, the sensor component 210 may be shaped and formed to improve the operation of the sensor. For example, in some embodiments, the sensor component 210 may utilize light-transmissive structures to improve the performance of a PPG sensor. For example, a light-transmissive structure may include a mask consisting of an opaque material that limits the aperture of one, some or all of the light source(s) and/or detector(s). In this way, the light-transmissive structures may selectively define or control a preferential volume of the user's body that light is emitted into and/or detected from.

Figure 3:
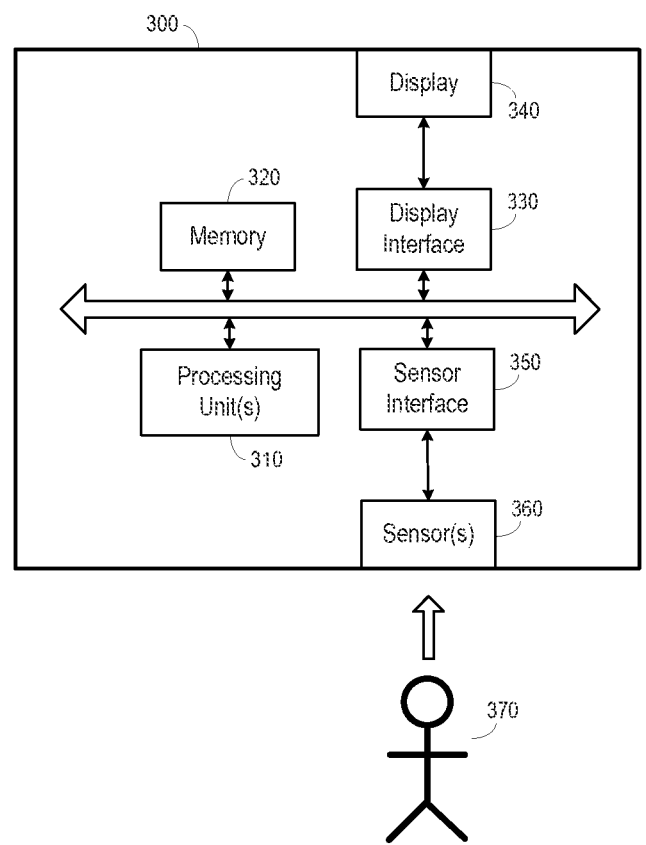
FIG. 3 is a block diagram of a device according to some embodiments.

FIG. 3 is a block diagram of a monitoring system 300 according to some embodiments. System 300 may be operated to control the collection and usage of biometric data pursuant to some embodiments. In some cases, the monitoring system 300 may implement internal features of the device 100 shown in FIG. 1.

As FIG. 3 shows, the system 300 includes one or more processing units 310 (e.g., hardware elements, such as processor cores and/or processing threads, discrete or integrated logic, and/or one or more state machines, and/or field programmable gate arrays (or combinations thereof)). In some cases, one or more processing units 310 are configured to execute processor-executable program code to cause the device 300 to operate as described herein, and memory 320 for storing the program code and any other suitable data. The memory 320 may comprise one or more fixed disks, solid-state random access memory, and/or removable media (e.g., a thumb drive) mounted in a corresponding interface (e.g., a USB port).

A display interface 330 provides communication with the display 340, which may comprise any system for visual presentation of information that is or becomes known. The display 340 may comprise a touch screen for receiving user input into the system 300 according to some embodiments. The display 140 shown in FIG. 1 is an example of the display 340.

One or more processing units 310 may execute processor-executable program code stored in memory 320 to cause the system 300 to process sensor data, control the operation of sensors and related components, and to perform operations as discussed herein. According to some embodiments, the system 300 comprises an integrated device such as, but not limited to, a wearable unit (e.g., around a user's wrist such as the device 100 shown in FIGS. 1 and 2, around the user's neck, or the like) or an otherwise portable unit (e.g., a smartphone, a dedicated music player, a fob). In some embodiments, elements of the system 300 may be embodied in separate devices, such as a server device (e.g., a desktop computer) including elements 310, 320 and 330, and a terminal device (e.g., a watch) including the display 340. The system 300 may perform functions other than those attributed thereto herein, and may include any elements that are necessary for the operation thereof.

Some embodiments of the system 300 include a portable monitoring device having a physical size and shape adapted to couple to the body of a user, which allows the user to perform normal or typical user activities (including, for example, exercise of all kinds and type) without hindering the user from performing such activities. An example of such a device is the device 100 of FIG. 1. The portable monitoring device may include a mechanism (for example, a clip, strap and/or tie) that facilitates coupling or affixing the device to the user during such normal or typical user activities.

The system 300 further includes one or more sensor interfaces 350 for exchanging data with one or more sensors 360. The sensors 360 may comprise any sensors for acquiring data including biometric monitoring data. Examples of sensors 360 include, but are not limited to, an accelerometer, a light sensor, a compass, a switch, a pedometer, a blood oxygen sensor, a gyroscope, a magnetometer, a Global Positioning System device, a proximity sensor, an altimeter, and a heart rate sensor. One or more of the sensors 360 may share common hardware and/or software components.

As shown in FIG. 3, a user 370 is pictured to indicate that, according to some embodiments, the user 370 influences the data acquired by one or more of the one or more sensors 360. For example, the one or more sensors 360 may generate data based on physical activity of the user 370. Moreover, one or more of sensors 360 may generate data via direct contact with the user, for example during heart rate, skin temperature, and/or blood oxygen monitoring.

Figure 4:
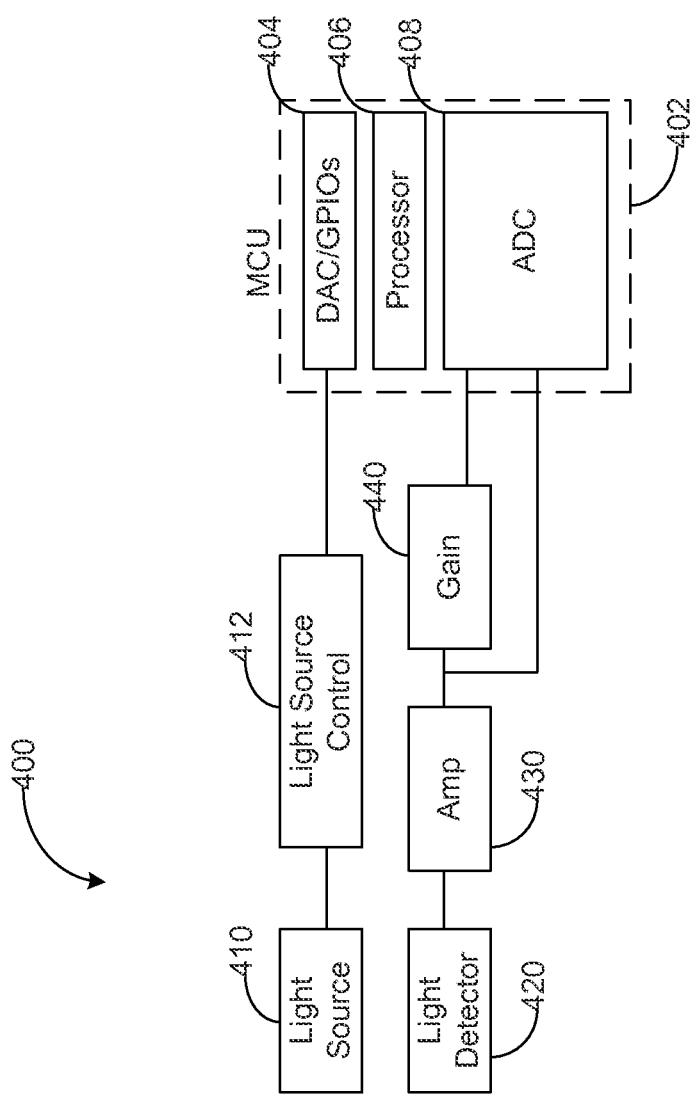
FIG. 4 is a block diagram of a sensor pursuant to some embodiments.

Reference is now made to FIG. 4, where an example block diagram of an optical heart rate sensor 400 is shown which may be used as one of multiple sensors 360 of the device 300 in FIG. 3. Although FIG. 4 is discussed relative to an optical heart rate sensor, it is to be appreciated that other embodiments may relate to other types of photoplethysmographic sensors. As shown in FIG. 4, the sensor 400 includes one or more light sources 410 which emit light toward a user's skin, and where the reflection and/or diffusion of such light from the skin/internal tissues of the user is sensed by one or more light detectors 420, the signal from which is subsequently digitized by an analog to digital converter ("ADC") 408. The intensity of the light source 410 may be modified (e.g., through a light source control module 412) to maintain a desired light signal intensity. For example, in some embodiments, the light source 410 may be controlled to place the light source 410 in one or several modes of operation, including an off mode of operation (where the light source 410 is disabled), a first mode of operation (where the light source 410 emits light at a low level of operation), and a second mode of operation (where the light source 410 emits light at a higher level of operation). In some embodiments, the high level of operation is approximately five times higher than the low level of operation, although the ratio between the two levels may be selected such that the ratio is not so low as to waste dynamic range of the amplifier 430 and not so large as to risk nearing the supply level voltage (which can cause problems with settling and noise). These modes of operations are discussed in greater detail below. Further, it is to be appreciated that the light source control module 412 and the microcontroller ("MCU") 402 may control the light source 410 at other modes of operation as well.

The light source control module 412 may be controlled by the MCU 402. As shown, the ADC 408 may be formed or configured as part of the MCU 402; however, such a configuration is for illustrative purposes only. Other possible implementations include the use of one or more internal or external ADCs or other components either implemented as a part of an MCU or separate therefrom. Because the MCU 402 obtains data from the first stage (the amplifier 430) and the second stage (the gain stage 440), the MCU 402 may be configured to switch between higher and lower gain (e.g., to accommodate a wide range of skin tone or the like). Further, in some operating conditions, the MCU 402 may effectively (or actually) cause the second stage 440 to be powered off or put in a low-power state when in a low gain mode of operation. The MCU 402 may adaptively control the operation of the light source 412 based on operating information received from the first and second stages (430, 440), allowing a wide variety of operating controls.

Pursuant to some embodiments, the detected light signal (obtained by the light detector 420) is processed using a low-gain amplifier 430 followed by a second gain stage 440. The output of both stages may be monitored by the MCU 402 to provide a wide range of gains suiting a wide range of users. When the second stage is in use (as described further herein), monitoring the first stage may provide valuable information for tuning the light source 410.

Features of the amplifier 430 and the gain stage 440 will now be described by referring to FIG. 5, where an example schematic of a circuit 500 is shown. As depicted, a low gain amplifier 530 has an output coupled to a capacitor 540 which may be selectively coupled to a switch 542. When the switch 542 is in the closed position, the amplifier 530 (also referred to herein as the "first stage") samples an ambient signal as a voltage across the capacitor 540. When the switch 542 is opened, a voltage representing the ambient signal is stored by capacitor 540. In operation, the control of the switch 542 is performed in conjunction with the control of the light source 410 to provide a sequence of operation in which the ambient is sampled as a voltage across the capacitor 540 while the switch 542 is closed. Then, the switch 542 is opened and the light source 410 is activated or enabled. This causes reflected light to be detected by light detector 420 providing a changed input to the amplifier 430 resulting in a corresponding change of V1 at the non-inverting input of amplifier 550. In particular, pursuant to some embodiments, the non-inverting input of amplifier 550 represents the voltage variation associated with the signal detected by light detector 420 less the ambient stored or frozen into the capacitor 540 (from when the switch 542 was closed, and prior to activation of the light source 410). The gain stage 440 (e.g., the amplifier 550 and feedback 552) provides additional gain to provide an output signal (Vout) representing the sampled PPG signal which is provided to an ADC 408 for further processing. In some embodiments, sequence of operation of the light source 410 may include operating the light source 410 to emit light at a low (non-zero) level for the ambient sampling.

Figure 6:
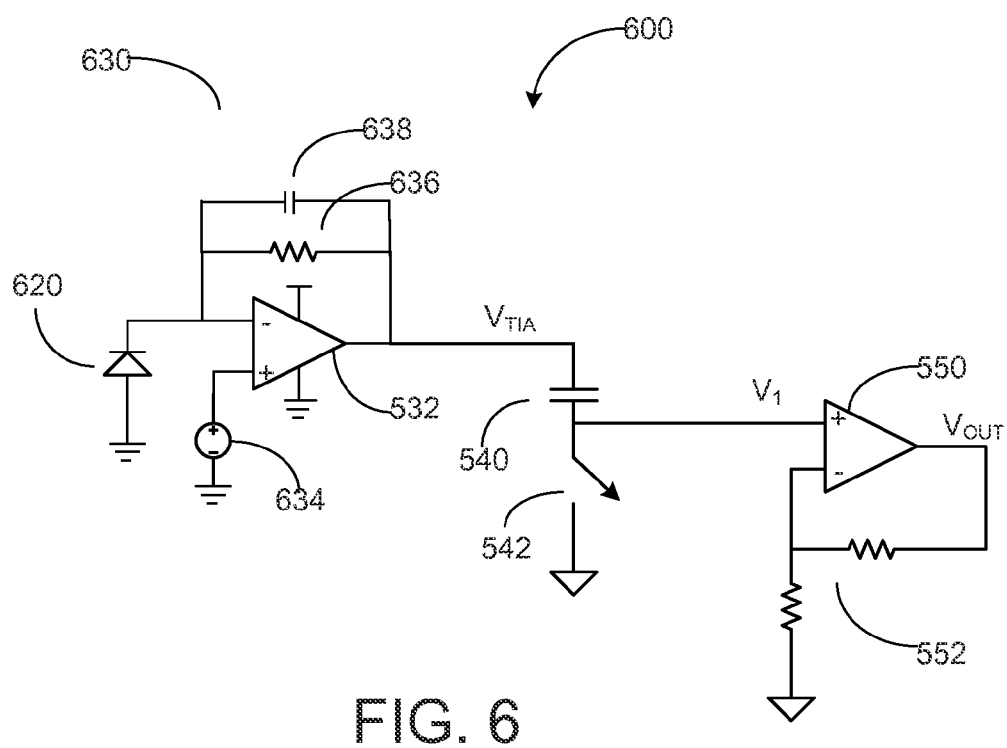
FIG. 6 is an example schematic of a circuit for a sensor pursuant to some embodiments.

One illustrative example of the configuration of the circuit 500 with a photodiode 620 and a voltage source 634 is shown in FIG. 6, although those skilled in the art will appreciate that other configurations may also be provided. In the configuration as depicted, a feedback resistor 636 is provided (e.g., to provide a gain of the amplifier 532 based on the resistance of the feedback resistor 636). A feedback capacitor 638 may be provided in parallel with the feedback resistor 636 to provide improved settling time and stability. A photodiode 620 is shown as the light detector, and is configured to provide a current path at the summing point of amplifier 532. The voltage source 634 is configured to provide a known and stable voltage to the non-inverting input of the amplifier 532 (such as, for example, 0.1-0.2 V, although the value may be adjusted to compensate for the expected signal magnitudes in a given implementation). In some embodiments, the voltage source 634 is configured using a schottky diode 620 rather than a voltage reference circuit. As described above, some embodiments utilize a low gain amplifier 532 to achieve desirable results such as higher dynamic range for rejecting strong sources of ambient light. Accordingly, the value of the feedback resistor 636 is selected to configure the amplifier 532 such that it has a low gain. The use of the voltage source 634 provides a non zero reference voltage to the amplifier 532 to prevent long settling times at signal levels near the supply voltage levels (which may be useful for some embodiments in low light situations). In some embodiments, it may be desirable to back-drive the amplifier 532 output (at VTIA) to a reference voltage, or clamp the photodiode to a zero or reverse-bias state when the amplifier 532 is off in order to reduce the amplifier's initial settling time. In some embodiments, this reference voltage back-drive may be achieved by coupling the output of the amplifier 532 to an input of the ADC 408 (as shown in FIG. 4). Further, in some embodiments, antialiasing filters may be provided at the output of the amplifier 532. A simple resistor/capacitor filter selected to operate near the sampling frequency of the ADC 408 may be preferred in some embodiments.

The control and sequencing of operation of the circuit of FIG. 5 will now be described by reference to FIG. 7 which shows the relative timing and illustrative order of magnitude of certain signals associated with the circuit of FIG. 5. For example, FIG. 5 shows the voltage from the amplifier 530

(VTIA), the state of the switch 542 (open or closed), the state of the light source 410 (on or off), the voltage at the non-inverting input of amplifier 550 (V1), and the output of the amplifier 550 (VOUT). Similar signals will also be described below in conjunction with FIGS. 8 and 9.

Figure 7:
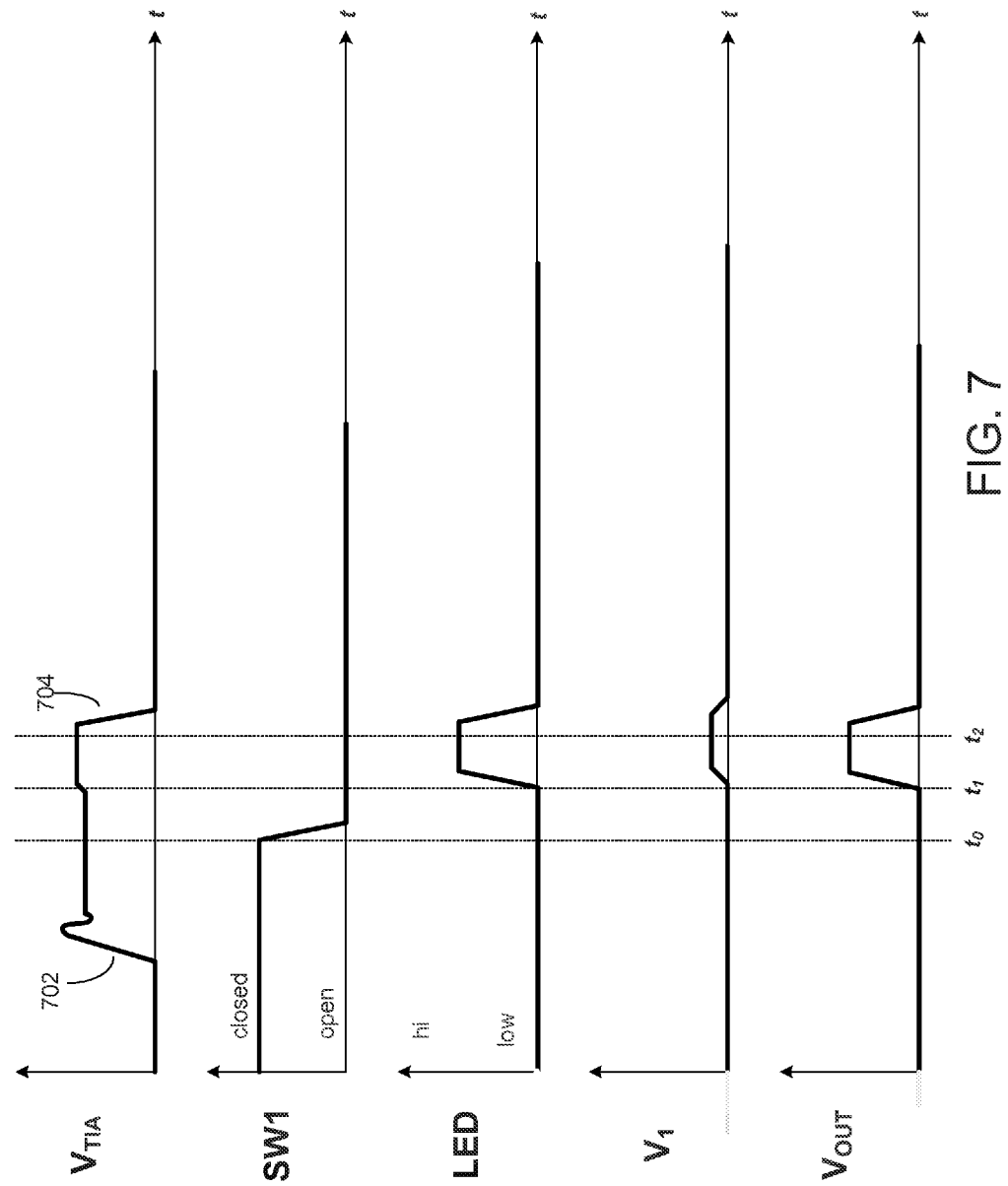
FIG. 7 is a diagram illustrating the relative timing and magnitude of certain signals associated with the circuits of FIGS. 3-5 pursuant to some embodiments.
Figure 8:
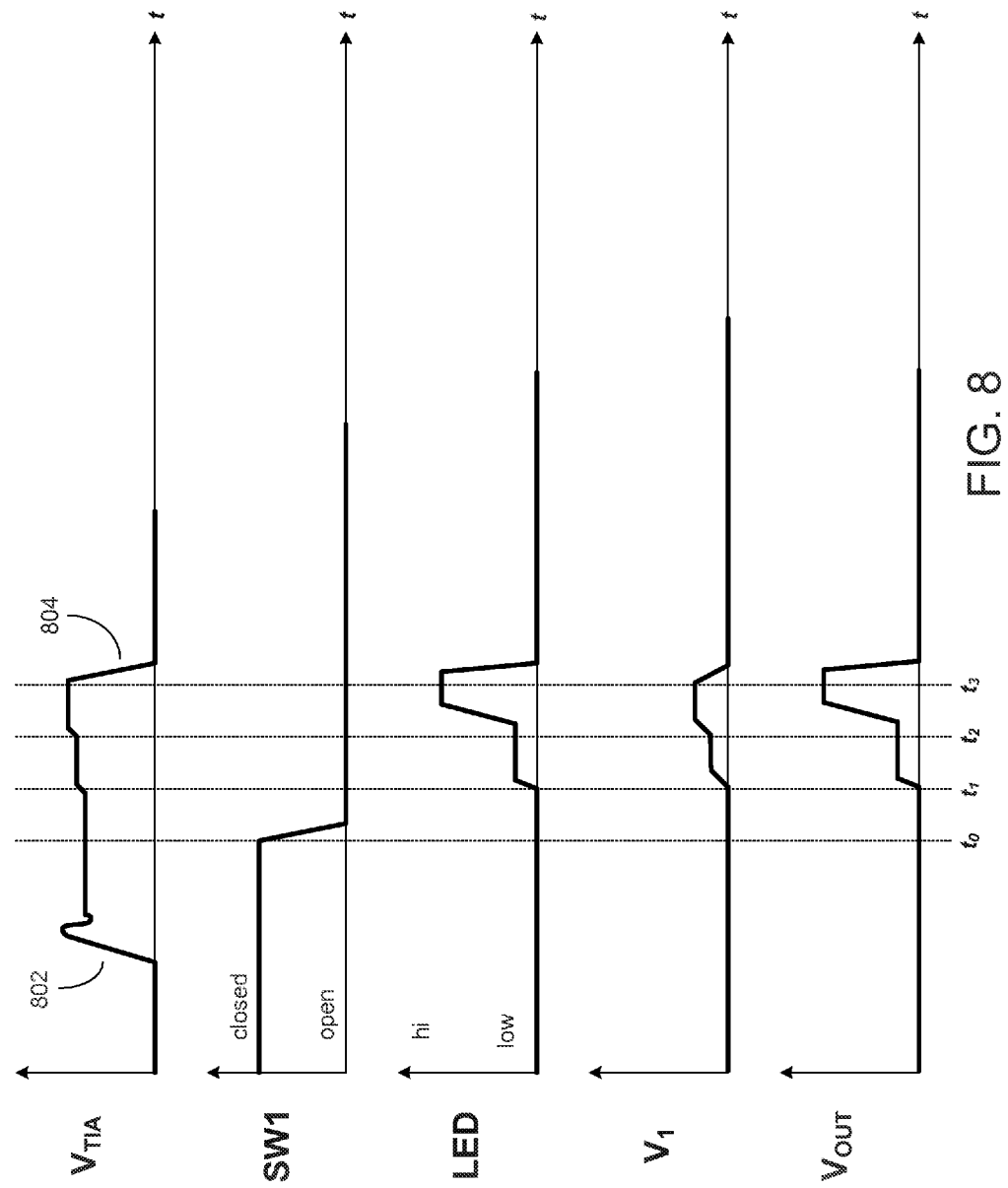
FIG. 8 is a diagram illustrating the relative timing and magnitude of certain signals associated with the circuits of FIGS. 3-5 pursuant to some embodiments.
Figure 9:
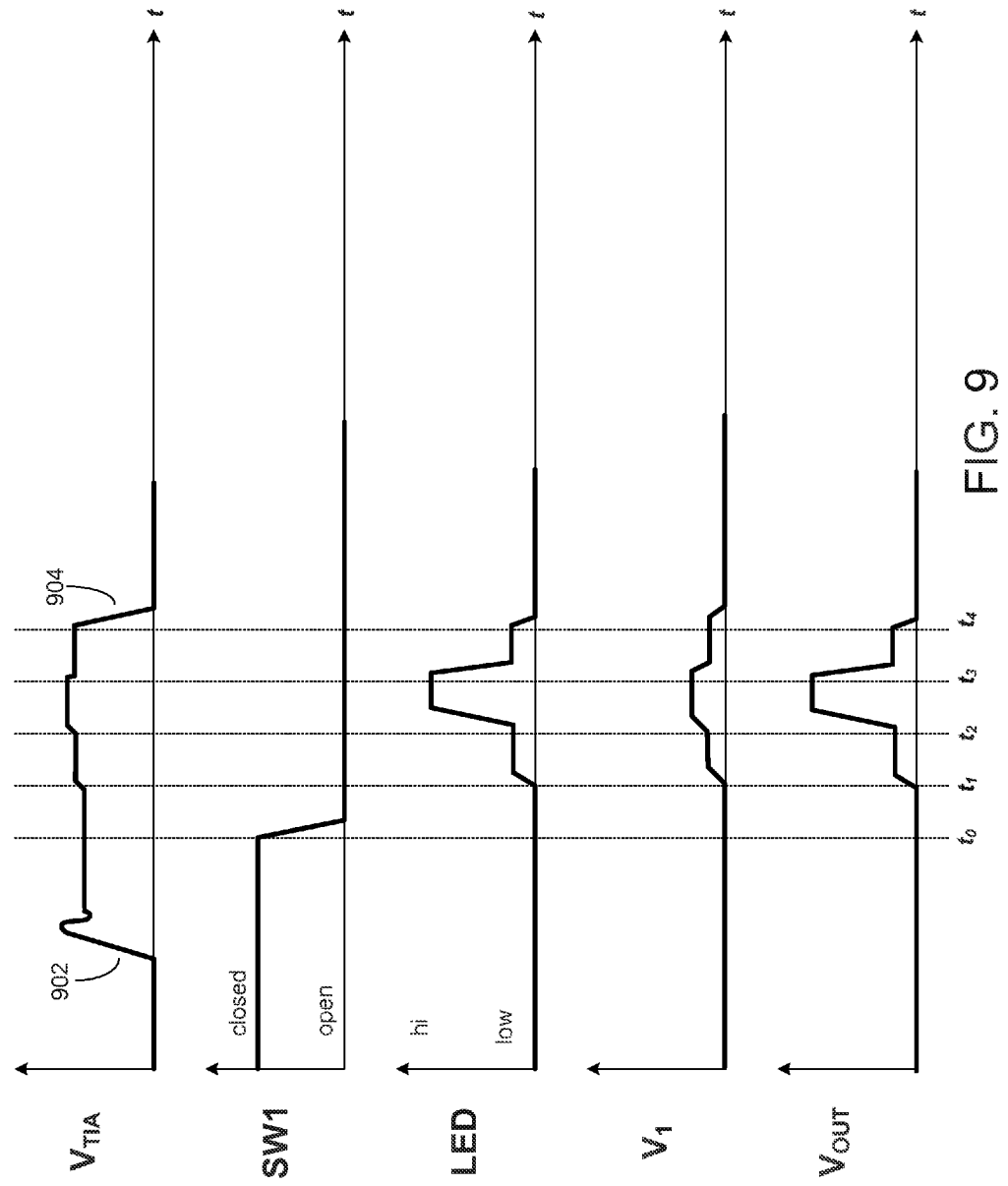
FIG. 9 is a diagram illustrating the relative timing and magnitude of certain signals associated with the circuits of FIGS. 3-5 pursuant to some embodiments.

Three primary time events are shown in the diagram of FIG. 7, times t0, t1 and t2, and depict the control of circuit 500 to perform basic ambient subtraction operations. Time t0 represents a time where the ambient is sampled as the voltage across capacitor 540 (while the switch 542 is closed). The switch 542 is then opened to freeze in or store the ambient signal across the capacitor 540. Time t1 represents a time where the light source 410 is activated or enabled, and time t2 represents a time where the output of the second stage 440 is sampled (e.g., the PPG output signal is sampled and provided to the ADC 408 for further processing). Also of note in FIG. 7 are events associated with the operation of the amplifier 430, including event 702 where the amplifier 430 is activated and event 704 where the amplifier 430 and the light source 410 are deactivated. Similar events are shown in FIGS. 8-9. The control events associated with the signals described in FIG. 7 (and FIGS. 8-9) may, for example, be controlled by the MCU 402 which was described in conjunction with FIG. 4. For example, the signals V1 and/or VOUT provided to the MCU 402 may be digitized by the ADC 408 at t2 and, in some embodiments, at t1.

Figure 5:
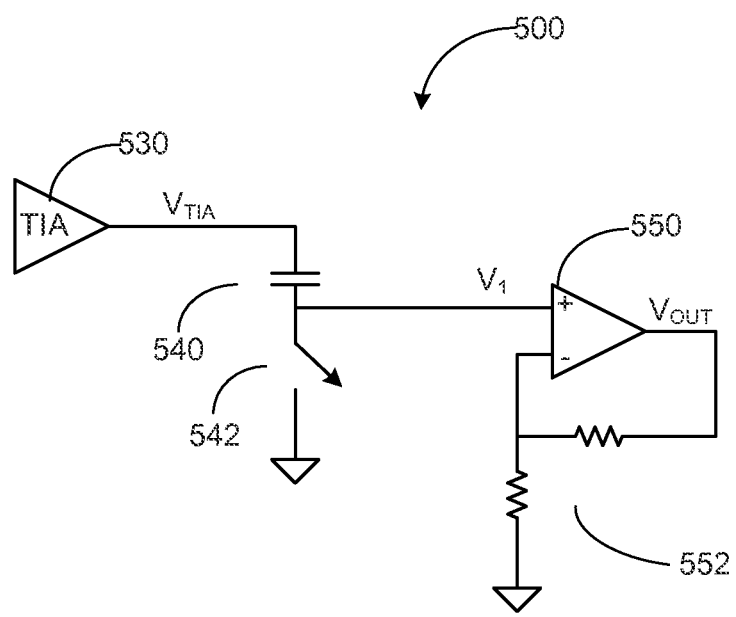
FIG. 5 is an example schematic of a circuit for a sensor pursuant to some embodiments.

Reference is now made to FIG. 8 where a further diagram is shown which depicts the operation of the circuit 500 of FIG. 5 to perform differential oversampling to generate an oversampled PPG output signal. Several primary time events are shown in the diagram of FIG. 8, including times t0, t1, t2 and t3. Time t0 represents a time where the ambient is sampled as the voltage across capacitor 540 (while the switch 542 is closed). The switch 542 is then opened to freeze in or store the ambient signal in the capacitor 540. Time t1 represents a time where the light source 410 is activated or enabled at a first level of operation (e.g., such as at a low level). Time t2 represents a time where the ambient-subtracted reflected light signal (detected by the light detector 420 and provided to the input of the amplifier 430) is sampled one or more times by an ADC. Time t3 represents a time where the light source 410 is enabled at a second level of operation (e.g., such as at a high level) and the ambient-subtracted reflected light signal (detected by the light detector 420 and provided at the input of the amplifier 430) is sampled one or more times by an ADC. For example, in some embodiments, ADC 408 may be a fast, low-precision ADC which uses oversampling of the ambient-subtracted signals. In some embodiments, higher-precision ADC(s) may also be used which operate on a single sample. The output signals (including the oversampling of the ambient-subtracted signals while the light source 410 is at a low level and while at the high level) are provided to the ADC 408 for further processing.

The differential oversampling illustrated in FIG. 8 allows the reduction of the effects of noise associated with the ambient and control signals, as the noise becomes a common-mode offset that is rejected by subtracting the high and low oversampled signals. For example, the differential oversampling illustrated in FIG. 8 allows the reduction of the effects 1/f noise or offset drift in the light source driver or receiver amplifiers, or charge injection from the switch 542 to the capacitor 540. Also, the two levels described in conjunction with the embodiment of FIG. 8 avoid operating the second stage near the supply rail voltages which otherwise might increase problems associated with increased settling times or PSRR (power supply rejection ratio). While the differential oversampling embodiment requires an additional mode of operation of the light source 410, the additional power requirements are minimized by operating the light source 410 at a low level of operation.

Features of a dynamic ambient rejection mode of operation will now be described by reference to FIG. 9. Several primary time events are shown in the diagram of FIG. 9, including times t0, t1, t2, t3 and t4. Time t0 represents a time where the ambient is sampled as the voltage across capacitor 540 (while the switch 542 is closed). The switch 542 is then opened to freeze in or store the ambient signal in the capacitor 540. Time t1 represents a time where the light source 410 is activated or enabled at a first level of operation (e.g., such as at a low level). Time t2 represents a time where the ambient-subtracted reflected light signal (detected by the light detector 420 and provided to the input of the amplifier 430) is oversampled (in the case where the ADC 408 is a low-precision ADC), or sampled (in the case where the ADC 408 is a higher-precision ADC). Time t3 represents a time where the light source 410 is enabled at a second level of operation (e.g., such as at a high level) and the ambient-subtracted reflected light signal (detected by the light detector 420 and provided at the input of the amplifier 430) is oversampled. The light source 410 is then activated or enabled (a second time) at the first level of operation (e.g., such as at the low level). Time t4 represents a time where the ambient-subtracted reflected light signal (detected by the light detector 420 and provided to the input of the amplifier 430) is oversampled. That is, in the dynamic ambient rejection mode of operation, the light source 410 is activated at two modes of operation (e.g., at a low level and a high level), and multiple PPG oversamples are taken (e.g., such as a first oversample at the low level of light source, a second oversample at the high level of light source, and a third oversample again at the low level of the light source).

The result is a mode of operation which allows rapidly changing ambient signals to be rejected. Biometric monitoring devices that are used in changing environments (such as a heart rate monitor used by a bicyclist or runner outdoors) must tolerate rapidly changing ambient light. When the device 400 is operated in a dynamic ambient rejection mode of operation, PPG samples are taken with a light emitter operating at a first (e.g., low) mode of operation before and after a PPG sample is taken with a light emitter operating at a second (e.g., high) mode of operation. This allows the MCU 402 to calculate a PPG value that considers the time changing nature of the ambient. For example, the MCU may generate a PPG value for the signals shown in FIG. 9 as follows: PPG=$-0.5*$ADC(t2)+ADC(t3)+($-0.5*$ADC(t4)) (where the times correspond to the time series shown in FIG. 9, and where the ADC value is the oversampled PPG signal value received at that point in time). Such embodiments provide desirable results in situations involving rapidly changing DC ambient signals, and allow both DC ambient and linearly changing DC ambient to be rejected. Pursuant to some embodiments, the values of both the first mode (e.g., low) and the second mode (e.g., high) of operation of the light source 410 are known by the MCU 402 and are controlled using the light source control 412.

Figure 10:
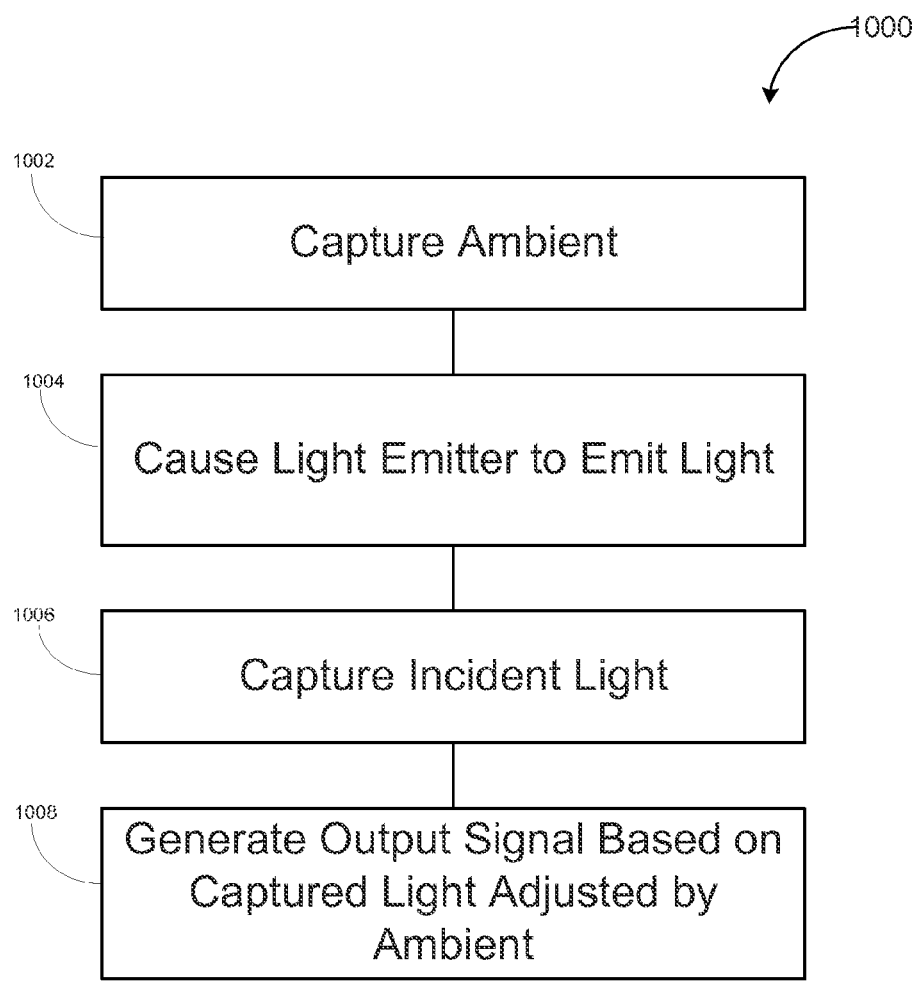
FIG. 10 is a flow diagram of a process according to some embodiments.

FIG. 10 is a flow diagram of process 1000 according to some embodiments. Process 1000 and the other processes described herein may be performed using any suitable combination of hardware or software, including implementations of system 300 or device 400. Software embodying these processes may be stored by any non-transitory tangible medium, including, for example, a read-only or read/write memory accessible to or embodied in the MCU 402 of FIG. 4. In general, process 1000 includes steps to control components such as those shown in FIG. 4 to capture signals for processing by a device such as an MCU 402. More particularly, the process 1000 depicts steps to control components to perform a basic ambient subtraction process (e.g., as described in conjunction with FIG. 7).

The control processing begins at 1002 where the components are controlled to capture a signal representing ambient conditions. For example, the MCU 402 may cause the amplifier 430 to operate to open a switch (such as switch 542) to freeze in or store a voltage representing the ambient conditions in a capacitor 540.

Processing continues at 1004 where the components are controlled to cause a light emitter to emit light. For example, the MCU 402 may cause the light source control 412 to activate the light source 410 to direct light having a known magnitude and intensity towards a user's skin. Processing continues at 1006 where the components are controlled to capture an incident light signal. For example, the MCU 402 may cause the operation of the light detector 420.

At 1008, the components are controlled to generate an output signal based on the captured light adjusted by the previously captured ambient signal. For example, the amplifier 430 may be operated to generate an intermediate output signal (shown as V1 in FIG. 5) which is based on the detected light signal less the stored value associated with the ambient signal captured at 1002. In some embodiments, processing at 1008 may include applying a gain to the intermediate output signal (e.g., using gain stage 440) before providing an output signal to an ADC 408 of the MCU 402. In this manner, embodiments allow accurate and low power measurement of optical signals (such as PPG signals).

Figure 11:
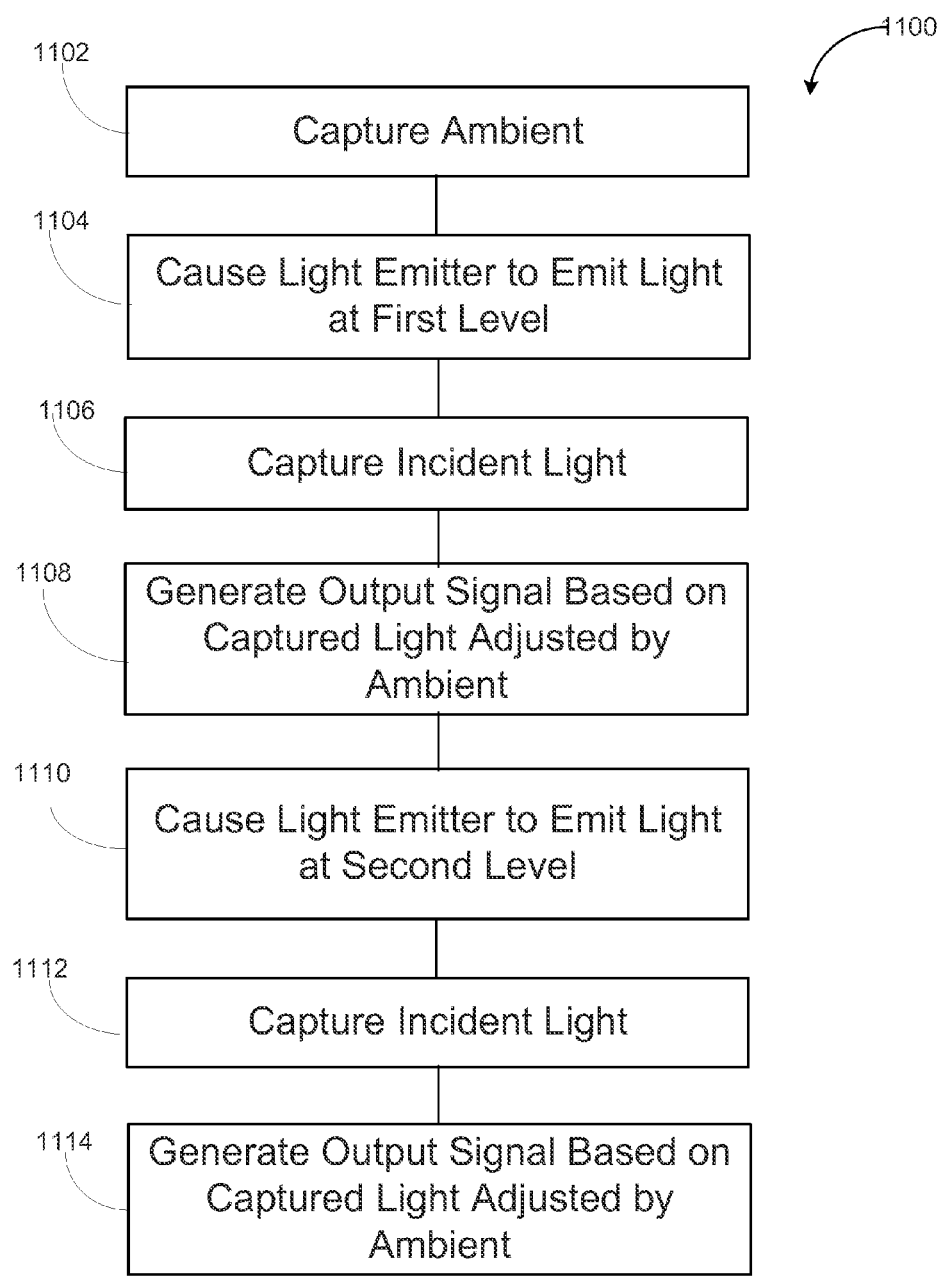
FIG. 11 is a flow diagram of a process according to some embodiments.

Reference is now made to FIG. 11 where a flow diagram of a further process 1100 pursuant to some embodiments is shown. The process 1100 depicts steps to control components to perform a differential oversampling process (e.g., as described in conjunction with FIG. 8).

The control processing begins at 1102 where the components are controlled to capture a signal representing ambient conditions. For example, the MCU 402 may cause the amplifier 430 to operate to open a switch (such as switch 542) to freeze in or store a voltage representing the ambient conditions in a capacitor 540.

Processing continues at 1104 where the components are controlled to cause a light emitter to emit light at a first level. For example, the MCU 402 may cause the light source control 412 to activate the light source 410 at a first mode of operation (e.g., such as at a known low intensity level) to direct light having a known magnitude and intensity towards a user's skin. Processing continues at 1106 where the components are controlled to capture an incident light signal. For example, the MCU 402 may cause the operation of the light detector 420.

At 1108, the components are controlled to generate an output signal based on the captured light adjusted by the previously captured ambient signal. For example, the amplifier 430 may be operated to generate an intermediate output signal (shown as V1 in FIG. 5) which is based on the detected light signal less the stored value associated with the ambient signal captured at 1102.

Processing continues at 1110 where the components are controlled to cause a light emitter to emit light at a second level. For example, the MCU 402 may cause the light source control 412 to activate the light source 410 at a second mode of operation (e.g., such as at a known high intensity level) to direct light having a known magnitude and intensity towards a user's skin. Processing continues at 1112 where the components are controlled to capture an incident light signal. For example, the MCU 402 may cause the operation of the light detector 420.

At 1114, the components are controlled to generate an output signal based on the captured light adjusted by the previously captured ambient signal. For example, the amplifier 430 may be operated to generate an intermediate output signal (shown as V1 in FIG. 5) which is based on the detected light signal less the stored value associated with the ambient signal captured at 1102. In this manner, the device of FIG. 4 may be operated to perform differential oversampling, providing additional data to the MCU 402 for processing heart rate information. The differential oversampling causes some sources of noise to appear as a common-mode offset which may be rejected by subtracting the low and high oversampled signals. The result is improved heart rate detection with greater accuracy at a relatively low additional cost (in terms of power, generally associated with the additional operation of the light source) over the process of FIG. 10. The MCU 402 may be configured to perform either differential oversampling (as described in FIG. 11) or basic ambient subtraction (as described in FIG. 10) in different environments or use cases, as the circuit (as shown in FIGS. 5 and 6) remain unchanged for either scenario.

Figure 12:
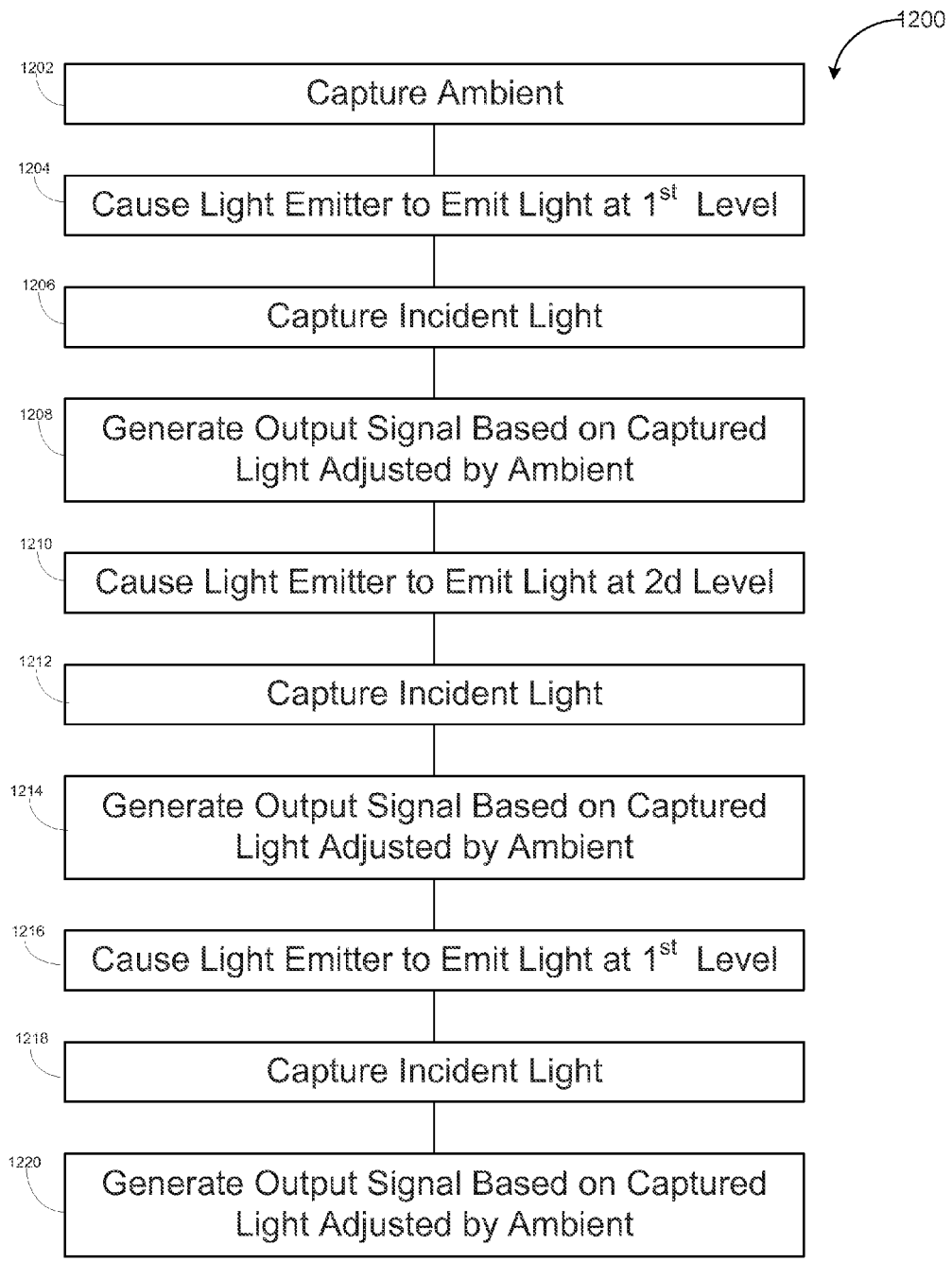
FIG. 12 is a flow diagram of a process according to some embodiments.

Reference is now made to FIG. 12 where a flow diagram of a further process 1200 pursuant to some embodiments is shown. The process 1200 depicts steps to control components to perform a dynamic ambient rejection process (e.g., as described in conjunction with FIG. 9).

The control processing begins at 1202 where the components are controlled to capture a signal representing ambient conditions. For example, the MCU 402 may cause the amplifier 430 to operate to open a switch (such as switch 542) to freeze in or store a voltage representing the ambient conditions in a capacitor 540.

Processing continues at 1204 where the components are controlled to cause a light emitter to emit light at a first level. For example, the MCU 402 may cause the light source control 412 to activate the light source 410 at a first mode of operation (e.g., such as at a known low intensity level) to direct light having a known magnitude and intensity towards a user's skin. Processing continues at 1206 where the components are controlled to capture an incident light signal. For example, the MCU 402 may cause the operation of the light detector 420.

At 1208, the components are controlled to generate an output signal based on the captured light adjusted by the previously captured ambient signal. For example, the amplifier 430 may be operated to generate an intermediate output signal (shown as V1 in FIG. 5) which is based on the detected light signal less the stored value associated with the ambient signal captured at 1202.

Processing continues at 1210 where the components are controlled to cause a light emitter to emit light at a second level. For example, the MCU 402 may cause the light source control 412 to activate the light source 410 at a second mode of operation (e.g., such as at a known high intensity level) to direct light having a known magnitude and intensity towards a user's skin. Processing continues at 1212 where the components are controlled to capture an incident light signal. For example, the MCU 402 may cause the operation of the light detector 420.

At 1214, the components are controlled to generate an output signal based on the captured light adjusted by the previously captured ambient signal. For example, the amplifier 430 may be operated to generate an intermediate output signal (shown as V1 in FIG. 5) which is based on the detected light signal less the stored value associated with the ambient signal captured at 1202.

Processing continues at 1216 where the components are controlled to cause the light emitter to emit light at the first level (e.g., the same level the light emitter was operated at in step 1204). For example, the MCU 402 may cause the light source control 412 to activate the light source 410 at a first mode of operation (e.g., such as at a known low intensity level) to direct light having a known magnitude and intensity towards a user's skin. Processing continues at 1218 where the components are controlled to capture an incident light signal. For example, the MCU 402 may cause the operation of the light detector 420.

At 1220, the components are controlled to generate an output signal based on the captured light adjusted by the previously captured ambient signal. For example, the amplifier 430 may be operated to generate an intermediate output signal (shown as V1 in FIG. 5) which is based on the detected light signal less the stored value associated with the ambient signal captured at 1202.

In this manner, the device of FIG. 4 may be operated to perform dynamic ambient rejection, providing additional data to the MCU 402 for processing heart rate information. The dynamic ambient rejection allows rapidly changing DC ambient to be handled. As discussed above in conjunction with FIG. 9, a formula may be applied by the MCU 402 to generate a PPG value that removes both the DC ambient and the rapidly changing DC ambient. The result is improved heart rate detection with greater accuracy in situations where the ambient conditions vary. The MCU 402 may be configured to perform either dynamic ambient rejection (as described in FIG. 12), differential oversampling (as described in FIG. 11) or basic ambient subtraction (as described in FIG. 10) in different environments or use cases, as the circuit (as shown in FIGS. 5 and 6) remain unchanged for either scenario. Each of the embodiments described herein allow accurate and low power generation of optical heart rate data.

The foregoing diagrams represent logical architectures for describing processes according to some embodiments, and actual implementations may include more or different components arranged in other manners. Other topologies may be used in conjunction with other embodiments. Moreover, each system described herein may be implemented by any number of devices in communication via any number of other public and/or private networks. Two or more of such computing devices may be located remote from one another and may communicate with one another via any known manner of network(s) and/or a dedicated connection. Each device may include any number of hardware and/or software elements suitable to provide the functions described herein as well as any other functions. For example, any computing device used in an implementation of some embodiments may include a processor to execute program code such that the computing device operates as described herein.

The modules and components described herein may be implemented in hardware, a processor executing firmware and/or software instructions, or any combination thereof. For instance, memory portions of processing modules may be implemented in one or more memory devices such as one or more of a magnetic disk, an optical disk, a random access memory (RAM), a video RAM, a Flash memory, etc. Similarly, processing units of processing or control modules (such as, for example, the light source control module 412 of FIG. 4) may be implemented using one or more of discrete components, an integrated circuit, an application-specific integrated circuit (ASIC), a programmable logic device (PLD), etc. If the module, processor and/or processing units are implemented using a processor executing firmware and/or software instructions, the software or firmware instructions may be stored in any computer readable memory such as on a magnetic disk, an optical disk, in a RAM or ROM or Flash memory, a memory of a processor (e.g., a cache memory), etc. The processor executing firmware and/or software instructions may comprise a general purpose processor or a special purpose processor such as a digital signal processor (DSP), a graphics processor, or the like.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A method for removing a component of a signal corresponding to ambient light in a photoplethysmographic sensor device, the method comprising:
    capturing, using a switch in a first position, a first detected light signal and holding the first detected light signal as voltage across a capacitor, the first detected light signal representing ambient light;
    causing a light emitter to generate a source light signal driven at a first level;
    capturing a second detected light signal, the second detected light signal representing the source light signal after interacting with a user's tissue;
    generating, using the switch in a second position, a first output signal based on the second detected light signal adjusted by the first detected light signal held in the capacitor;
    changing the light emitter to generate a source light signal driven at a second level that is different than the first level;
    capturing a third detected light signal, the third detected light signal representing the source light signal driven at the second level after interacting with the user's tissue;
    generating, using the switch in the second position, a second output signal based on the third detected light signal adjusted by the first detected light signal held in the capacitor; and
    changing the light emitter again to generate the source light signal driven at the first level and capturing a fourth detected light signal representing the source light signal driven at the first level interacting with the user's tissue;
    generating a third output signal based on the fourth detected light signal adjusted by the first detected light signal held in the capacitor; and
    generating a photoplethysmographic signal based on a weighted combination of the first, second, and third output signals,
    wherein initially detected ambient light is removed during the generating of the first, second, and third output signals, and dynamic changing ambient light is removed as a result of the weighted combination of the first, second, and third output signals.

2. The method of claim 1, wherein the photoplethysmographic signal is generated based on a first difference between a weighted combination of the first and second output signals and a second difference between the first difference and the third output signal that has been weighted.

3. The method of claim 1, wherein the capturing of the first detected light signal further comprises:
   activating a light detector to detect the first detected light signal, wherein the first detected light signal represents at least one of (i) an ambient light condition, and (ii) an ambient light condition and a light signal representing a source light signal driven at non-zero level after interacting with the user's tissue.

4. The method of claim 1, wherein the first output signal is generated at an output of an amplifier, the amplifier receiving a first input based on the second detected light signal adjusted by the first detected light signal.

5. The method of claim 4, wherein the amplifier is an adjustable gain amplifier.

6. The method of claim 4, further comprising:
   deactivating the light emitter after generation of the first output signal.

7. The method of claim 1, further comprising:
   converting the first output signal to a digital signal representing a voltage for processing by a processor.

8. The method of claim 1, wherein the first output signal and the second output signal are generated at different times at an output of an amplifier, the amplifier receiving a first input at a first time based on the second detected light signal adjusted by the first detected light signal to generate the first output signal, and the amplifier receiving a second input at a second time based on the third detected light signal adjusted by the first detected light signal to generate the second output signal.

9. The method of claim 1, wherein the source light signal driven at the second level is a higher level than the first level.

10. The method of claim 8, further comprising:
    deactivating the light emitter after generation of the second output signal.

11. The method of claim 1, further comprising:
    converting the second output signal to a second digital signal representing a voltage for processing by a processor.

12. The method of claim 1, wherein the first output signal, the second output signal and the third output signal are generated at different times at an output of an amplifier, the amplifier receiving a first input at a first time based on the second detected light signal adjusted by the first detected light signal to generate the first output signal, the amplifier receiving a second input at a second time based on the third detected light signal adjusted by the first detected light signal to generate the second output signal, and the amplifier receiving a third input at a third time based on the fourth detected light signal adjusted by the first detected light signal to generate the third output signal.

13. The method of claim 1, wherein the source light signal driven at the first level is a low level, and the source light signal driven at the second level is a high level, where the high level is at least twice the low level.

14. The method of claim 12, further comprising:
    deactivating the light emitter after generation of the third output signal.

15. The method of claim 1, further comprising:
    converting the third output signal to a third digital voltage signal for processing by a processor.

16. A method performed by a photoplethysmographic sensor device, the method comprising:
    causing a light emitter to generate a source light signal driven at a first level;
    measuring a first detected light signal, the first detected light signal representing the source light signal driven at the first level interacting with a user's skin, and subtracting ambient light from the first detected light signal to generate a first output signal;
    increasing the source light signal driven by the light emitter to a second level;
    measuring a second detected light signal, the second light signal representing the source light signal increased to the second level interacting with the user's skin, and subtracting ambient light from the second detected light signal to generate a second output signal;
    decreasing the source light signal driven by the light emitter back to the first level;
    measuring a third detected light signal representing the source light signal driven at the first level interacting with the user's skin, and subtracting ambient light from the third detected light signal to generate a third output signal; and
    generating a photoplethysmographic sample based on a weighted combination of the first, second, and third output signals, wherein dynamic changing ambient light is removed as a result of the weighted combination of the first, second, and third output signals.

17. A non-transitory computer-readable medium storing executable instructions for removing a component of a signal corresponding to ambient light in a photoplethysmographic sensor device, the instructions, when executed, cause one or more processors to:
    capture, using a switch in a first position, a first detected light signal and holding the first detected light signal as voltage across a capacitor, the first detected light signal representing ambient light;
    cause a light emitter to generate a source light signal driven at a first level;
    capture a second detected light signal, the second detected light signal representing the source light signal interacting with a user's tissue;
    generate, using the switch in a second position, a first output signal based on the second detected light signal adjusted by the first detected light signal held in the capacitor;
    change the light emitter to generate a source light signal driven at a second level that is different than the first level;
    capture a third detected light signal, the third detected light signal representing the source light signal driven at the second level interacting with the user's tissue;
    generate, using the switch in the second position, a second output signal based on the third detected light signal adjusted by the first detected light signal held in the capacitor;
    change the light emitter again to generate the source light signal driven at the first level and capture a fourth detected light signal representing the source light signal driven at the first level interacting with the user's tissue;
    generate a third output signal based on the fourth detected light signal adjusted by the first detected light signal held in the capacitor; and
    generate a photoplethysmographic signal based on a weighted combination of the first, second, and third output signals,
    wherein initially detected ambient light is removed during the generating of the first, second, and third output signals, and dynamic changing ambient light is removed as a result of the weighted combination of the first, second, and third output signals.

18. The computer readable medium of claim 17, wherein the instructions further cause, when executed, the one or more processors to:
    activate a light detector to detect the first detected light signal.

19. The computer readable medium of claim 17, wherein the instructions further cause, when executed, the one or more processors to:
    deactivate the light emitter after generation of the first output signal, the second output signal and the third output signal.

20. The computer readable medium of claim 17, wherein the source light signal driven at the first level is a low level, and the source light signal driven at the second level is a high level different from the low level.

21. The computer readable medium of claim 17, wherein the instructions further cause, when executed, the one or more processors to:
    convert the first output signal, the second output signal, and the third output signal to digital voltage signals for processing by a processor.

22. The computer readable medium of claim 17, wherein the instructions further cause, when executed, the one or more processors to:
    generate a heart rate signal after removing a common-mode offset between the first and second output signals.

23. A photoplethysmographic sensor device, comprising:
    one or more processors;
    non-transitory, computer readable medium storing instructions, which when executed, cause the one or more processors to:
        cause a light emitter to generate a source light signal driven at a first level;
        measure a first detected light signal, the first detected light signal representing the source light signal driven at the first level after interacting with a user's skin, and subtract ambient light from the first detected light signal to generate a first output signal;
        increase the source light signal driven by the light emitter to a second level;
        measure a second detected light signal, the second light signal representing the source light signal increased to the second level after interacting with the user's skin, and subtract ambient light from the second detected light signal to generate a second output signal;
        decrease the source light signal driven by the light emitter back to the first level;
        measure a third detected light signal representing the source light signal driven at the first level interacting with the user's skin, and subtract ambient light from the third detected light signal to generate a third output signal; and
        generate a photoplethysmographic sample based on a weighted combination of the first, second, and third output signals, wherein dynamic changing ambient light is removed as a result of the weighted combination of the first, second, and third output signals.

24. The photoplethysmographic sensor device of claim 23, further comprising:
    at least a first light detector configured to detect the source light signal after interacting with the user's skin, the at least first light detector providing a signal representing the detected source light signal to a first circuit stage including a low gain amplifier.

25. The photoplethysmographic sensor device of claim 24, further comprising:
    a gain stage circuit coupled to receive an output of the first circuit stage and to apply a gain to the output of the first circuit stage.

\* \* \* \* \*